United States Patent
Ma et al.

(10) Patent No.: US 12,005,050 B2
(45) Date of Patent: Jun. 11, 2024

(54) METHODS FOR PREVENTING OR TREATING H. PYLORI INFECTION

(71) Applicant: TENNOR THERAPEUTICS (SUZHOU) LIMITED, Suzhou (CN)

(72) Inventors: Zhenkun Ma, Suzhou (CN); Guozhu Geng, Suzhou (CN); Jing Chen, Suzhou (CN); Yu Liu, Suzhou (CN); Xiangyi Xu, Suzhou (CN); Changlin Ai, Suzhou (CN); Junlei Zhang, Suzhou (CN); Ting Song, Suzhou (CN); Shuangshuang Zhao, Suzhou (CN)

(73) Assignee: TENNOR THERAPEUTICS (SUZHOU) LIMITED, Suzhou (CN)

(*) Notice: Subject to any disclaimer, the term of this patent is extended or adjusted under 35 U.S.C. 154(b) by 0 days.

(21) Appl. No.: 18/363,006

(22) Filed: Aug. 1, 2023

(65) Prior Publication Data
US 2024/0082229 A1  Mar. 14, 2024

(30) Foreign Application Priority Data
Aug. 18, 2022  (WO) ................ PCT/CN2022/113421

(51) Int. Cl.
| A61K 31/439 | (2006.01) |
| A61K 9/28 | (2006.01) |
| A61K 9/48 | (2006.01) |
| A61K 31/43 | (2006.01) |
| A61K 31/4439 | (2006.01) |
| A61P 31/04 | (2006.01) |

(52) U.S. Cl.
CPC ............ *A61K 31/439* (2013.01); *A61K 9/28* (2013.01); *A61K 9/48* (2013.01); *A61K 31/43* (2013.01); *A61K 31/4439* (2013.01); *A61P 31/04* (2018.01)

(58) Field of Classification Search
CPC .......... A61K 31/439; A61K 9/28; A61K 9/48; A61K 31/43; A61K 31/4439; A61P 31/04
USPC ........................................... 514/278
See application file for complete search history.

(56) References Cited

U.S. PATENT DOCUMENTS

2020/0093807 A1* 3/2020 Ma .................. A61K 9/4858

FOREIGN PATENT DOCUMENTS

| CN | 104971061 |   | 10/2015 |
| CN | 106822119 |   | 6/2017 |
| CN | 109453165 | A * | 3/2019 |
| WO | WO 2008/008480 |   | 1/2008 |

OTHER PUBLICATIONS

Chevy et al, ACG Clinical Guideline: Treatment of Helicobacter pylori Infection, Am J Gastroenterol 2017; 112:212-238 (Year: 2017).*
Wikipedia, Omeprazole, Oct. 2021, p. 1-13 (Year: 2021).*
International Search Report issued May 4, 2023, in PCT/CN2022/113421 filed Aug. 18, 2022.

(Continued)

*Primary Examiner* — Taylor V Oh
(74) *Attorney, Agent, or Firm* — Oblon, McClelland, Maier & Neustadt, L.L.P.

(57) ABSTRACT

The present disclosure provides methods, drug combinations and kits for treating, ameliorating, reversing and/or preventing a *Helicobacter pylori* (*H. pylori*) infection in a patient in need thereof.

14 Claims, 3 Drawing Sheets

(56) References Cited

OTHER PUBLICATIONS

Zhenkun Ma et al., "Design, Synthesis, and Characterization of TNP-2198, a Dual-Targeted Rifamycin-Nitroimidazole Conjugate with Potent Activity Against Microaerophilic and Anaerobic Bacterial Pathogens," *J. Med. Chem.* (2022), 65, 4481-4495.

Jiarong Chen, et al., "Recent Advances in Hybrid Antibacterial Agents," *Chinese Journal of Pharmaceuticals*, 48 (9), 2017, pp. 1233-1245, w/English Abstract.

\* cited by examiner

METHODS FOR PREVENTING OR TREATING *H. PYLORI* INFECTION

BACKGROUND OF THE INVENTION

*Helicobacter pylori* is a major causative pathogen of chronic gastritis, peptic ulcer, gastric mucosal associated lymphoma (MALT) lymphoma, and gastric cancer, and was classified as a class I carcinogen by the World Health Organization's International Agency for Research on Cancer (WHO/IARC) in 1994. Globally, more than half of adults are infected with *Helicobacter pylori*, the vast majority of people infected with *Helicobacter pylori* have chronic gastritis, about 10% of the infected people develop peptic ulcers, and 1-3% of those infected with *Helicobacter pylori* develop stomach cancer. The prevalence of *Helicobacter pylori* infection in adult populations in China is 40%-60%. According to the WHO/IARC 2014 World Cancer Report, the number of newly reported cases of stomach cancer in China in 2012 was 405,600, accounting for 42.6% of the number of new cases worldwide, and about 325,400 people died of stomach cancer in China in 2012. A large number of clinical studies have shown that the eradication of *Helicobacter pylori* can effectively prevent the recurrence of peptic ulcers and the occurrence of stomach cancer.

There are many problems associated with the current therapies for *Helicobacter pylori* eradication. Due to the emergence and development of antimicrobial resistance, the eradication rate of standard triple therapies (clarithromycin, amoxicillin and proton pump inhibitors) has been declining, from the initial 90% to the current 50-70%. In China, the problem of antimicrobial resistance is even more serious, with high resistance rates for the three most widely used antimicrobial drugs for eradicating *Helicobacter pylori* (metronidazole 40-70%, clarithromycin 20-50%, levofloxacin 20-50%). In order to improve the eradication rate, the expert consensus report published in 2016 in China recommends the use of bismuth quadruple therapy as first-line therapy in China. A recent large scale clinical trial in China showed that the eradication rate of bismuth quadruple therapy was only 72.9%.

Accordingly, there is an urgent need to develop new therapies for eradicating *Helicobacter pylori*, especially therapies capable of addressing the drug resistance problems.

SUMMARY OF THE INVENTION

The present disclosure provides new methods and products (e.g., drug combinations and/or kits) for treating, ameliorating, reversing and/or preventing *Helicobacter pylori* (*H. pylori*) infection. The methods and products of the present disclosure are highly effective in eradicating *H. pylori*, including drug resistant *H. pylori*.

In one aspect, the present disclosure provides a method for treating, ameliorating, reversing and/or preventing a *Helicobacter pylori* (*H. pylori*) infection in a patient in need thereof. The method comprises administering to said patient: an effective amount of compound I 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin, or a pharmaceutically acceptable salt thereof; and an effective amount of an acid blocker.

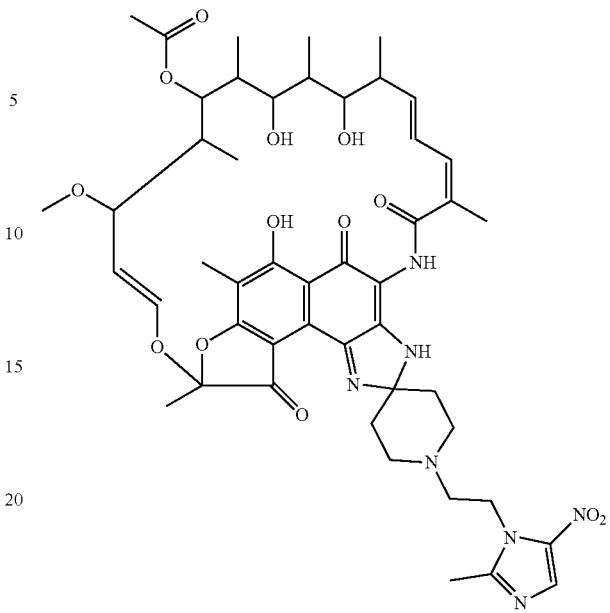

In some embodiments, the compound I is the compound of Formula 1
Formula 1.
In some embodiments, the compound I is 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin S.

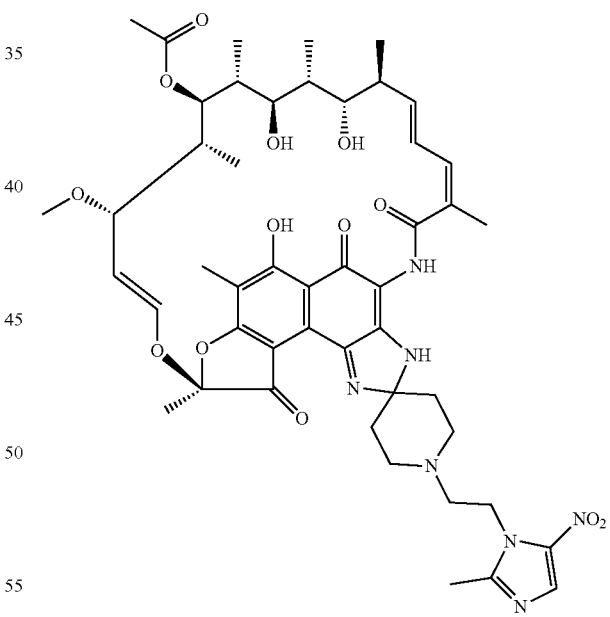

In some embodiments, the compound I is the compound of Formula 2
Formula 2.
In some embodiments, the compound I is administered to the patient at a dose of about 400 mg to about 600 mg, twice per day (BID) or three times per day (TID).
In some embodiments, the compound I is administered to the patient for 7-14 consecutive days.
In some embodiments, each time, the compound I is administered to the patient after meal.

In some embodiments, the compound I is administered in one or more dosage units, and each the dosage unit comprises about 100 mg to about 400 mg of the compound I.

In some embodiments, the compound I is administered as a capsule or a tablet.

In some embodiments, the acid blocker is a proton pump inhibitor (PPI).

In some embodiments, the acid blocker is administered to the patient at a dose of about 10 mg to about 40 mg, twice per day (BID) or three times per day (TID).

In some embodiments, the acid blocker is administered to the patient for at least 7-14 consecutive days.

In some embodiments, the acid blocker is administered as an enteric-coated tablet.

In some embodiments, each enteric-coated tablet comprises about 10 mg to about 20 mg of the acid blocker.

In some embodiments, the acid blocker is selected from the group consisting of: rabeprazole sodium, esomeprazole magnesium, omeprazole, lansoprazole, pantoprazole sodium and ilaprazole.

In some embodiments, the acid blocker is administered together with the compound I to the patient.

In some embodiments, the method further comprises administering to the patient an effective amount of an additional antibiotic.

In some embodiments, the additional antibiotic is selected from the group consisting of: rifabutin, clarithromycin, amoxicillin, metronidazole, levofloxacin, tetracycline and furazolidone.

In some embodiments, the additional antibiotic is administered to the patient at a dose of about 100 mg to about 1000 mg, twice per day (BID) or three times per day (TID).

In some embodiments, the additional antibiotic is administered to the patient for 7-14 consecutive days.

In some embodiments, the additional antibiotic is administered to the patient after meal.

In some embodiments, the additional antibiotic is administered as a capsule or a tablet. In some embodiments, each capsule or tablet comprises about 100 mg to about 500 mg of the additional antibiotic.

In some embodiments, the additional antibiotic is amoxicillin.

In some embodiments, the additional antibiotic is administered together with the compound I and the acid blocker to the patient.

In some embodiments, the *Helicobacter pylori* is resistant to one or more antibiotics selected from the group consisting of clarithromycin, amoxicillin, metronidazole, levofloxacin, tetracycline, furazolidone and rifabutin.

In some embodiments, the *Helicobacter pylori* is resistant to rifabutin and/or metronidazole.

In another aspect, the present disclosure provides a drug combination. The drug combination comprises an effective amount of compound I 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin, or a pharmaceutically acceptable salt thereof; and an effective amount of an acid blocker.

In some embodiments of the drug combination, the compound I is the compound of Formula 1

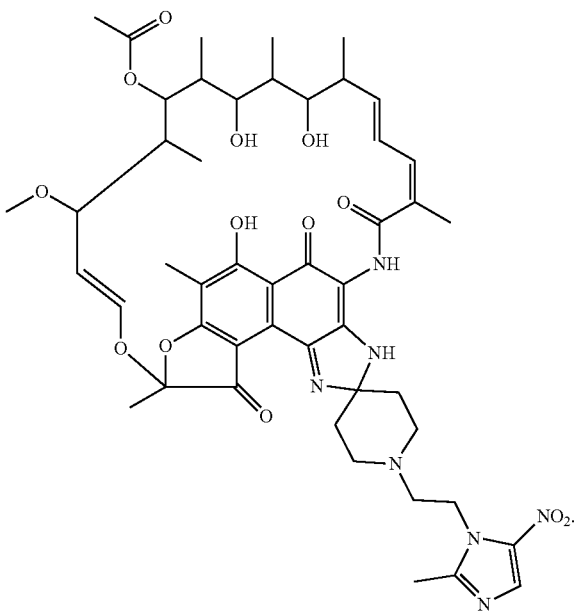

Formula 1

In some embodiments of the drug combination, the compound I is 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin S.

In some embodiments of the drug combination, the compound I is the compound of Formula 2

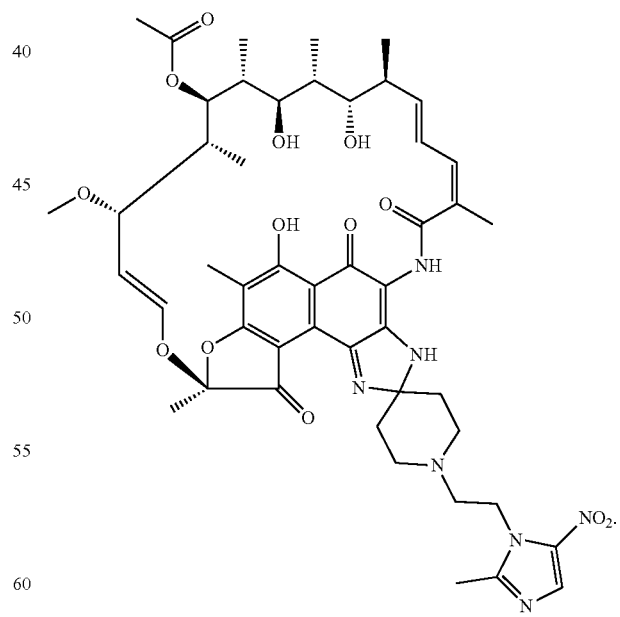

Formula 2

In some embodiments of the drug combination, the compound I is comprised in an amount suitable to be administered at a dose of about 400 mg to about 600 mg, twice per day (BID) or three times per day (TID).

In some embodiments of the drug combination, the compound I is comprised in an amount suitable to be administered for 7-14 consecutive days.

In some embodiments of the drug combination, the compound I is comprised in the form of a capsule or a tablet. In some embodiments of the drug combination, each capsule or tablet comprises about 100 mg to about 400 mg of the compound I.

In some embodiments of the drug combination, the acid blocker is a proton pump inhibitor (PPI).

In some embodiments of the drug combination, the acid blocker is comprised in an amount suitable to be administered at a dose of about 10 mg to about 40 mg, twice per day (BID) or three times per day (TID).

In some embodiments of the drug combination, the acid blocker is comprised in an amount suitable to be administered for at least 7-14 consecutive days.

In some embodiments of the drug combination, the acid blocker is comprised in the form of an enteric-coated tablet.

In some embodiments of the drug combination, each enteric-coated tablet comprises about 10 mg to about 20 mg of the acid blocker.

In some embodiments of the drug combination, the acid blocker is selected from the group consisting of: rabeprazole sodium, esomeprazole magnesium, omeprazole, lansoprazole, pantoprazole sodium and ilaprazole.

In some embodiments, the drug combination further comprises an effective amount of an additional antibiotic.

In some embodiments of the drug combination, the additional antibiotic is selected from the group consisting of: rifabutin, clarithromycin, amoxicillin, metronidazole, levofloxacin, tetracycline and furazolidone.

In some embodiments of the drug combination, the additional antibiotic is comprised in an amount suitable to be administered at a dose of about 100 mg to about 1000 mg, twice per day (BID) or three times per day (TID).

In some embodiments of the drug combination, the additional antibiotic is comprised in an amount suitable to be administered for 7-14 consecutive days.

In some embodiments of the drug combination, the additional antibiotic is comprised in the form of a capsule or a tablet. In some embodiments, each capsule or tablet comprises about 100 mg to about 500 mg of the additional antibiotic.

In some embodiments of the drug combination, the additional antibiotic is amoxicillin.

In another aspect, the present disclosure provides a kit, comprising the drug combination of the present disclosure.

In some embodiments, the kit further comprises an instruction for applying the method of the present disclosure.

In another aspect, the present disclosure provides use of an effective amount of a compound I 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin or a pharmaceutically acceptable salt thereof and an effective amount of an acid blocker in the manufacture of a medicament for treating, ameliorating, reversing and/or preventing a *Helicobacter pylori* (*H. pylori*) infection in a patient in need thereof.

In another aspect, the present disclosure provides use of the drug combination of the present disclosure or the kit of the present disclosure in the manufacture of a medicament for treating, ameliorating, reversing and/or preventing a *Helicobacter pylori* (*H. pylori*) infection in a patient in need thereof.

In some embodiments, the *Helicobacter pylori* is resistant to one or more antibiotics selected from the group consisting of clarithromycin, amoxicillin, metronidazole, levofloxacin, tetracycline, furazolidone and rifabutin.

In some embodiments, the *Helicobacter pylori* is resistant to rifabutin and/or metronidazole.

In another aspect, the present disclosure provides a drug combination of the present disclosure or a kit of the present disclosure, for use in treating, ameliorating, reversing and/or preventing a *Helicobacter pylori* (*H. pylori*) infection in a patient in need thereof. In some embodiments, the *Helicobacter pylori* is resistant to one or more antibiotics selected from the group consisting of clarithromycin, amoxicillin, metronidazole, levofloxacin, tetracycline, furazolidone and rifabutin. In some embodiments, the *Helicobacter pylori* is resistant to rifabutin and/or metronidazole.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "FIG.", "Fig." and "FIG." herein), of which:

DETAILED DESCRIPTION

Figure 1:
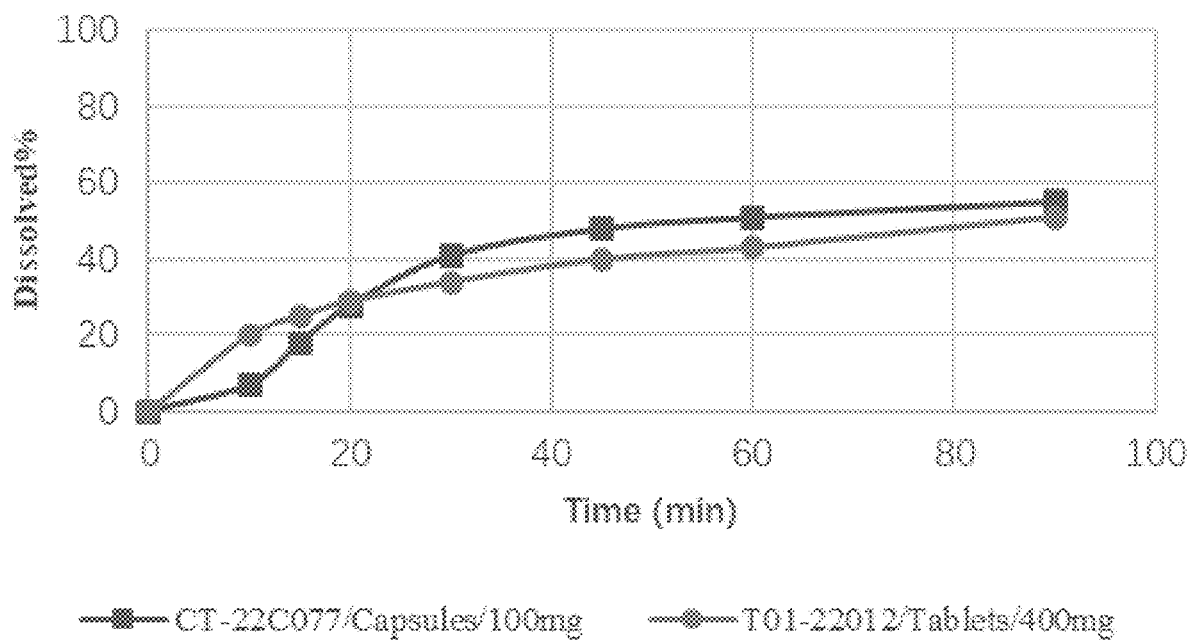
FIGS. 1-3 demonstrate comparison of dissolution profiles of different dosage forms and strengths.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the term "antibiotic", "antimicrobial compound" and "antibiotic agent" are used interchangeably and generally refers to a compound or composition which decreases the viability of a microorganism, or which inhibits the growth or reproduction of a microorganism. "Inhibits the growth or reproduction" means increasing the generation cycle time by at least 2-fold, e.g., at least 10-fold, at least 100-fold or even indefinitely, as in total cell death. An antibiotic may be a naturally occurring, semisynthetic, or fully synthetic agent which is capable of inhibiting the growth of microbes (i.e., bacteria, fungi, viruses, parasites and microbial spores) thereby preventing their development and microbial or pathogenic action. An antibiotic agent can be selected from the group consisting of small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. As used herein, an "antibiotic" is intended to embrace antibacterial agent or antimicrobial agent, antifungal agent, antiprotozoal agent, antiviral agent and mixtures thereof.

As used herein, the term "acid blocker" generally refers to an agent capable of reducing the amount, the secretion and/or the effect of an acid (e.g., stomach acid) in a patient.

As used herein, the term "drug combination" generally refers to a pharmaceutical product (e.g., a medical prescription) containing two or more active ingredients. The two or more active ingredients may be comprised in a single composition, in a single package, in independent and separate compositions, or in separate packages.

As used herein, the term "dosage unit" generally refers to physically discrete units that are suitable for administration as a single dose to a patient, with each unit of it containing a predetermined amount of an active ingredient (e.g., compound I) calculated to be capable of producing the desired therapeutic effect together with a desired pharmaceutical carrier, diluent, or excipient. In some embodiments, the unit dose is a single formulation. In some embodiments, the unit dose comprises one or more media such that each media comprises an effective amount of at least one of said active ingredient together with a pharmaceutically acceptable carrier and excipient. In some embodiments, the unit dose is one or more tablets, capsules, pills, or patches administered simultaneously to the patient.

As used herein, the term "(being) administered together with" generally means that two or more therapeutic agents may be co-administered to the patients in a mixture, simultaneously administered as single agents, or administered sequentially as a single agent in any order.

As used herein, the term "effective amount" generally refers to an amount necessary for producing a desired result, such as preventing, reducing, reversing, or alleviating a symptom of a disease or disorder. Sometimes, a desired result may include enhancing the bioavailability of another medicament or compound. Sometimes, a desired result may include the favorable treatment of a disease state or condition. The term effective encompasses both an amount or concentration of one or more active agent(s) as described herein and a period of time which is consistent with producing an intended effect.

As used herein, the term "*Helicobacter pylori* (*H. pylori*) infection" generally refers to the presence of an abnormal level or activity of *H. pylori*. A patient may be classified as having an *H. pylori* infection if *H. pylori* whole organisms, *H. pylori* genes, *H. pylori* proteins, *H. pylori* protein activity (e.g., urease activity) or human antibodies specific for *H. pylori* proteins or lipids are detected in the patient's tissues (tissue biopsies, blood, stool, saliva, etc.).

As used herein, the term "kit" generally refers to a collection or combination of materials, compositions and/or articles (such as tools, containers or devices). A kit may also include instructions for using the kit. Different components of a kit may be packaged and provided separately.

As used herein, the term "pharmaceutically acceptable salt" generally refers to a salt of a compound that does not cause significant irritation to a patient to which it is administered and does not abrogate the biological activity and properties of the compound.

As used herein, the term "proton pump inhibitor" or "PPI" generally refers to an agent capable of blocking, inhibiting or reducing the activity of the hydrogen-potassium adenosine triphosphatase enzyme (H, K-ATPase) system in a patient (e.g., on the luminal surface), thereby preventing or inhibiting the secretion of acids in the patient.

As used herein, the term "resistance" or "drug-resistance" generally refers to a reduction in effectiveness of a medicament such as an antimicrobial or an antibiotic in preventing or treating a disease or disorder. When an organism is resistant to more than one drug, it may be characterized as multidrug-resistant.

As used herein, the term "patient" includes living organisms in which a disease or disorder may occur. The term "patient" includes animals (e.g., mammals (e.g., cats, dogs, horses, pigs, cows, goats, sheep, rodents (e.g., mice or rats), rabbits, squirrels, bears, primates (e.g., chimpanzees, monkeys, gorillas, and humans)), as well as avian (e.g. chickens, ducks, Peking ducks, geese), and transgenic species thereof. In some cases, the patient is a human or a non-human primate (e.g., chimpanzee, monkey, macaque, gorilla). In certain cases, the patient is a human being.

Unless expressly stated or apparent from the context, as used herein, the term "about" is understood to be within the normal variation ranges, e.g., within 2 standard deviations of the mean. It can be understood to be within 10%, 9%, 8%, 7%, 6%, 5%, 4%, 3%, 2%, 1%, 0.5%, 0.1%, 0.05%, or 0.01% of the indicated value.

Unless otherwise specified, "a", "an", "the" and "at least one" are used interchangeably and refer to one or more than one.

In the present disclosure, the term "comprise" also encompasses "is", "has" and "consist of". For example, "a composition comprising X and Y" may be understood to encompass a composition that comprises at least X and Y. It shall also be understood to disclose a composition that only comprises X and Y (i.e., a composition consisting of X and Y).

In one aspect, the present disclosure provides a method for treating, ameliorating, reversing and/or preventing a *Helicobacter pylori* (*H. pylori*) infection in a patient in need thereof. The method comprises administering to said patient: an effective amount of compound I 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin, or a pharmaceutically acceptable salt thereof; and an effective amount of an acid blocker.

In another aspect, the present disclosure provides a drug combination. The drug combination comprises an effective amount of compound I 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin, or a pharmaceutically acceptable salt thereof; and an effective amount of an acid blocker.

In another aspect, the present disclosure provides a kit. The kit comprises the drug combination of the present disclosure.

In another aspect, the present disclosure provides use of an effective amount of compound I 4-Deoxy-3,4-[2-spiro-[1-[2-(2-methyl-5-nitro-imidazol-1-yl)ethyl]-piperidin-4- yl]]-(1H)-imidazo-(2,5-dihydro)rifamycin or a pharmaceutically acceptable salt thereof and an effective amount of an acid blocker in the manufacture of a medicament for treating, ameliorating, reversing and/or preventing a *Helicobacter pylori* (*H. pylori*) infection in a patient in need thereof.

In another aspect, the present disclosure provides use of the drug combination or the kit of the present disclosure in the manufacture of a medicament for treating, ameliorating, reversing and/or preventing a *Helicobacter pylori* (*H. pylori*) infection in a patient in need thereof.

In some cases, the method of the present disclosure further comprises administering to said patient an effective amount of an additional antibiotic.

In some cases, the drug combination of the present disclosure further comprises an effective amount of an additional antibiotic.

Compound I

The compound I of the present disclosure may be the compound of Formula 1

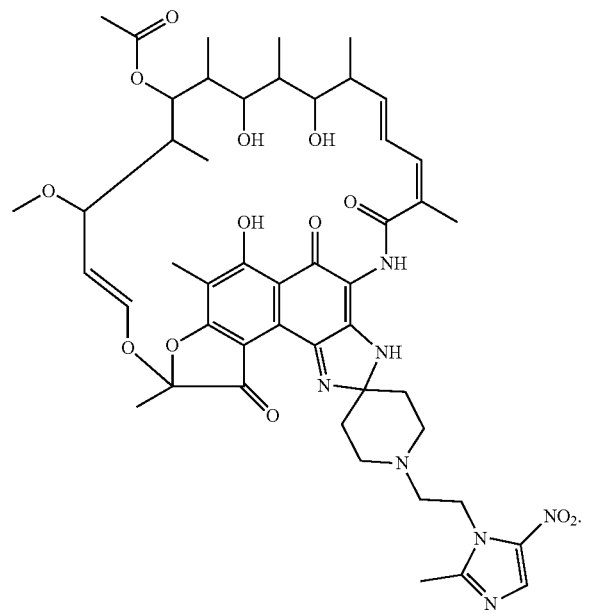 [SMILES: COC1/C=C/OC2(C)Oc3c(C)c(O)c4c(c3C2=O)C2=NC3(CCN(CCn5c([N+](=O)[O-])cnc5C)CC3)NC2=C(NC(=O)/C(C)=C\C=C\C(C)C(O)C(C)C(O)C(C)C(OC(C)=O)C1C)C4=O]

(Formula 1)

In some cases, the compound I is (9S,12E,14S,15R,16S, 17R,18R,19R,20S,21S,22E,24Z)-16-(Acetyloxy)-6,18,20-trihydroxy-14-methyoxy-7,9,15,17,19,21,25-heptamethyl-1'-[2-(2-methyl-5-nitro-imidazol-1-yl)ethyl]spiro[9,4-(epoxypentadeca[1,11,13]trienimino)-2H-furo[2',3':7,8]naphth[1,2-d]imidazole-2,4'-piperidine]-5,10,26(3H,9H)-trione.

In some embodiments, the compound I is 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin.

In some embodiments, the compound I has the CAS number of 1001314-13-1.

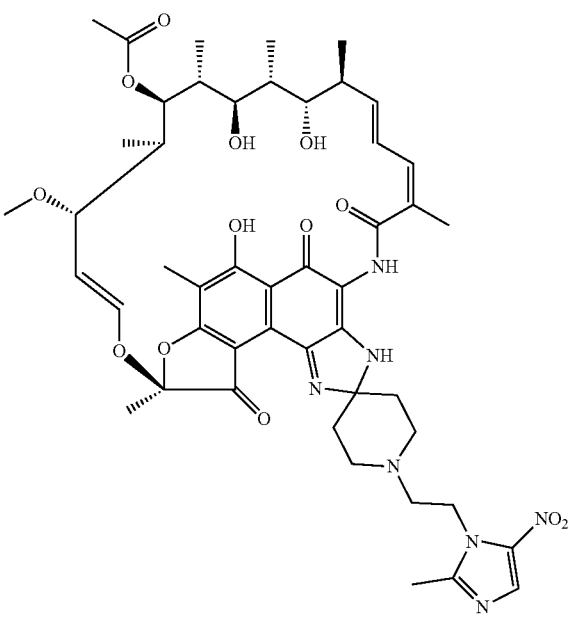 [SMILES: CO[C@H]1/C=C/O[C@@]2(C)Oc3c(C)c(O)c4c(c3C2=O)C2=NC3(CCN(CCn5c([N+](=O)[O-])cnc5C)CC3)NC2=C(NC(=O)/C(C)=C\C=C\[C@H](C)[C@H](O)[C@@H](C)[C@@H](O)[C@@H](C)[C@H](OC(C)=O)[C@@H]1C)C4=O]

In some embodiments, the compound I has the structure of Formula 2 (Formula 2).

In some embodiments, the compound I has the structure of Formula 3, * is the chiral center (Formula 3).

The compound I may be administered to the patient at a dose of about 400 mg to about 600 mg, twice per day (BID) or three times per day (TID). In some embodiments, the compound I is administered to the patient at a dose of about 400 mg/time to about 600 mg/time (e.g., about 400 mg/time, about 450 mg/time, about 500 mg/time, about 550 mg/time or about 600 mg/time), twice per day. In some embodiments, the compound I is administered to the patient at a dose of about 400 mg/time to about 600 mg/time (e.g., about 400 mg/time, about 450 mg/time, about 500 mg/time, about 550 mg/time or about 600 mg/time), three times per day.

The compound I may be administered to the patient for 7-14 consecutive days. For example, the compound I may be administered to the patient for 7, 8, 9, 10, 11, 12, 13 or 14 consecutive days, For example, the compound I may be administered to the patient at a dose of about 400 mg/time to about 600 mg/time (e.g., about 400 mg/time, about 450 mg/time, about 500 mg/time, about 550 mg/time, about 600 mg/time), twice per day, for 7, 8, 9, 10, 11, 12, 13 or 14 consecutive days.

For example, the compound I may be administered to the patient at a dose of about 400 mg/time to about 600 mg/time (e.g., about 400 mg/time, about 450 mg/time, about 500 mg/time, about 550 mg/time, about 600 mg/time), three times per day, for 7, 8, 9, 10, 11, 12, 13 or 14 consecutive days.

In some embodiments, the compound I is administered to the patient at a dose of about 400 mg/time, twice per day, for 7, 8, 9, 10, 11, 12, 13 or 14 consecutive days.

In some embodiments, the compound I is administered to the patient at a dose of about 600 mg/time, twice per day, for 7, 8, 9, 10, 11, 12, 13 or 14 consecutive days.

In some embodiments, the compound I is administered to the patient at a dose of about 400 mg/time, three times per day, for 7, 8, 9, 10, 11, 12, 13 or 14 consecutive days.

In some embodiments, the compound I is administered to the patient at a dose of about 600 mg/time, three times per day, for 7, 8, 9, 10, 11, 12, 13 or 14 consecutive days.

The compound I may be administered to the patient before meal, together with meal or after meal. In some embodiments, each time, the compound I is administered to the patient after meal.

The compound I may be administered to the patient as one or more (e.g., 1, 2, 3, 4, 5, 6, 7, 8, 9, 10 or more) dosage units. Each dosage unit may comprise about 10 mg to about 600 mg (e.g., about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg) of said compound I.

A dosage unit may be a capsule or a tablet. For example, a dosage unit may be a capsule comprising about 10 mg to about 600 mg (e.g., about 100 mg to about 400 mg, such as 100 mg, 200 mg, 300 mg or 400 mg) said compound I. For example, a dosage unit may be a tablet comprising about 10 mg to about 600 mg (e.g., about 100 mg to about 400 mg, such as 100 mg, 200 mg, 300 mg or 400 mg) said compound I.

Acid Blocker

The acid blocker may be a proton pump inhibitor (PPI). For example, the acid blocker may be selected from the group consisting of: rabeprazole sodium, esomeprazole magnesium, omeprazole, lansoprazole, pantoprazole sodium and ilaprazole.

The acid blocker may be administered to the patient at a dose of about 10 mg to about 40 mg (e.g., about 10 mg, about 15 mg, about 20 mg, about 25 mg, about 30 mg, about 35 mg, about 40 mg).

The acid blocker may be administered to the patient twice per day (BID) or three times per day (TID).

For example, the acid blocker (e.g., the PPI, such as the rabeprazole sodium) may be administered to the patient at a dose of about 10 mg to about 40 mg (such as about 20 mg)/time, twice per day.

For example, the acid blocker (e.g., the PPI, such as the rabeprazole sodium) may be administered to the patient at a dose of about 10 mg to about 40 mg (such as about 20 mg)/time, three times per day.

For example, the acid blocker may be administered to the patient for at least 7-14 (e.g., at least 7, at least 8, at least 9, at least 10, at least 11, at least 12, at least 13, or at least 14) consecutive days.

In some embodiments, the acid blocker (e.g., the PPI, such as the rabeprazole sodium) is administered to the patient at a dose of about 10 mg to about 40 mg (such as about 20 mg)/time, twice per day, for at least 7-14 (e.g., at least 7, at least 8, at least 9, at least 10, at least 11, at least 12, at least 13, or at least 14) consecutive days.

In some embodiments, the acid blocker (e.g., the PPI, such as the rabeprazole sodium) is administered to the patient at a dose of about 10 mg to about 40 mg (such as about 20 mg)/time, three times per day, for at least 7-14 (e.g., at least 7, at least 8, at least 9, at least 10, at least 11, at least 12, at least 13, or at least 14) consecutive days.

The acid blocker may be administered to the patient as one or more (e.g., 1, 2, 3, 4, 5, 6, 7, 8, 9, 10 or more) dosage units. Each dosage unit may comprise about 10 mg to about 50 mg (e.g., about 10 mg, about 15 mg, about 20 mg, about 25 mg, about 30 mg, about 35 mg, about 40 mg) of said acid blocker.

A dosage unit may be a capsule or a tablet. For example, a dosage unit may be a capsule comprising about 10 mg to about 50 mg (e.g., about 10 mg to about 40 mg, such as 10 mg, 20 mg, 30 mg, 40 mg or 50 mg) said acid blocker (e.g., the PPI, such as the rabeprazole sodium). For example, a dosage unit may be a tablet (such as an enteric-coated tablet) comprising about 10 mg to about 50 mg (e.g., about 10 mg to about 40 mg, such as 10 mg, 20 mg, 30 mg, 40 mg or 50 mg) said acid blocker (e.g., the PPI, such as the rabeprazole sodium).

The acid blocker (e.g., the PPI, such as the rabeprazole sodium) may be administered before, together with, or after the administration of the compound I. In some embodiments, the acid blocker (e.g., the PPI, such as the rabeprazole sodium) is administered together with the compound I to the patient.

Each time, the acid blocker (e.g., the PPI, such as the rabeprazole sodium) may be administered before, together with, or after meal (e.g., breakfast, lunch and/or dinner).

Additional Antibiotics

According to any aspect of the present disclosure, the additional antibiotic may be selected from the group consisting of: rifabutin, clarithromycin, amoxicillin, metronidazole, levofloxacin, tetracycline and furazolidone.

In some embodiments, the additional antibiotic comprises two or more agents selected from: rifabutin, clarithromycin, amoxicillin, metronidazole, levofloxacin, tetracycline and furazolidone. For example, the additional antibiotic may comprise an effective amount of amoxicillin and an effective amount of clarithromycin. For example, the additional antibiotic may comprise an effective amount of amoxicillin and an effective amount of levofloxacin. For example, the additional antibiotic may comprise an effective amount of amoxicillin and an effective amount of furazolidone. For example, the additional antibiotic may comprise an effective amount of tetracycline and an effective amount of metronidazole. For example, the additional antibiotic may comprise an effective amount of tetracycline and an effective amount of furazolidone. For example, the additional antibiotic may comprise an effective amount of amoxicillin and an effective amount of metronidazole. For example, the additional antibiotic may comprise an effective amount of amoxicillin and an effective amount of tetracycline.

The additional antibiotic may be administered to said patient at a dose (each separately or combined) of about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The additional antibiotic may be administered to the patient once per day, twice per day (BID), three times per day (TID) or four times per day.

For example, the additional antibiotic may comprise amoxicillin. The amoxicillin may be comprised or administered at an effective amount or dose. The effective amount of amoxicillin may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The amoxicillin may be administered to the patient twice per day (BID) or three times per day (TID). In some embodiments, the amoxicillin is administered to the patient at a dose of about 1000 mg/time, and it is administered to the patient twice or three times per day. In some embodiments, the amoxicillin is administered to the patient at a dose of about 1000 mg/time, and it is administered to the patient twice per day.

In some cases, the additional antibiotic may comprise rifabutin. The rifabutin may be comprised or administered at an effective amount or dose. The effective amount of rifabutin may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The rifabutin may be administered to the patient once per day, twice per day (BID) or three times per day (TID). In some embodiments, the rifabutin is administered to the patient at a dose of about 100 mg/time to about 300 mg/time, and it is administered to the patient once, twice or three times per day. In some embodiments, the rifabutin is administered to the patient at a dose of about 150 mg/time, and it is administered to the patient twice per day. In some embodiments, the rifabutin is administered to the patient at a dose of about 300 mg/time, and it is administered to the patient once per day.

For example, the additional antibiotic may comprise clarithromycin. The clarithromycin may be comprised or administered at an effective amount or dose. The effective amount of clarithromycin may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The clarithromycin may be administered to the patient twice per day (BID) or three times per day (TID). In some embodiments, the clarithromycin is administered to the patient at a dose of about 500 mg/time, and it is administered to the patient twice or three times per day. In some embodiments, the clarithromycin is administered to the patient at a dose of about 500 mg/time, and it is administered to the patient twice per day.

For example, the additional antibiotic may comprise metronidazole. The metronidazole may be comprised or administered at an effective amount or dose. The effective amount of metronidazole may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The metronidazole may be administered to the patient three times per day or four times per day. In some embodiments, the metronidazole is administered to the patient at a dose of about 400 mg/time, and it is administered to the patient three times per day. In some embodiments, the metronidazole is administered to the patient at a dose of about 400 mg/time, and it is administered to the patient four times per day.

For example, the additional antibiotic may comprise levofloxacin. The levofloxacin may be comprised or administered at an effective amount or dose. The effective amount of levofloxacin may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The levofloxacin may be administered to the patient once per day or twice per day. In some embodiments, the levofloxacin is administered to the patient at a dose of about 500 mg/time, and it is administered to the patient once per day. In some embodiments, the levofloxacin is administered to the patient at a dose of about 200 mg/time, and it is administered to the patient twice per day.

For example, the additional antibiotic may comprise furazolidone. The furazolidone may be comprised or administered at an effective amount or dose. The effective amount of furazolidone may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The furazolidone may be administered to the patient once per day or twice per day. In some embodiments, the furazolidone is administered to the patient at a dose of about 100 mg/time, and it is administered to the patient twice per day.

For example, the additional antibiotic may comprise tetracycline. The tetracycline may be comprised or administered at an effective amount or dose. The effective amount of tetracycline may be about 100 mg to about 1000 mg (e.g., about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg). The tetracycline may be administered to the patient three times per day or four times per day. In some embodiments, the tetracycline is administered to the patient at a dose of about 500 mg/time, and it is administered to the patient three times per day. In some embodiments, the tetracycline is administered to the patient at a dose of about 500 mg/time, and it is administered to the patient four times per day.

The additional antibiotic may be administered to the patient for 7-14 consecutive days (e.g., for 7 consecutive days, for 8 consecutive days, for 9 consecutive days, for 10 consecutive days, for 11 consecutive days, for 12 consecutive days, for 13 consecutive days, for 14 consecutive days).

In some embodiments, the additional antibiotic is or comprises amoxicillin, it is administered to the patient at a dose of about 1000 mg/time, it is administered twice or three times per day, and it is administered to the patient for 7-14 consecutive days.

The additional antibiotic may be administered to the patient before meal, together with meal, or after meal. In some embodiments, each time, the additional antibiotic is administered to the patient after meal (e.g., breakfast, lunch or dinner).

The additional antibiotic may be administered to the patient as one or more (e.g., 1, 2, 3, 4, 5, 6, 7, 8, 9, 10 or more) dosage units. Each dosage unit may comprise about 100 mg to about 500 mg (e.g., about 100 mg, about 150 mg, about 200 mg, about 250 mg, about 300 mg, about 350 mg, about 400 mg, about 450 mg, or about 500 mg) of said additional antibiotic (e.g., amoxicillin).

A dosage unit may be a capsule or a tablet. For example, a dosage unit may be a capsule comprising about 100 mg to about 500 mg (e.g., about 100 mg, about 150 mg, about 200 mg, about 250 mg, about 300 mg, about 350 mg, about 400 mg, about 450 mg, or about 500 mg) said additional antibiotic (e.g., amoxicillin). For example, a dosage unit may be a tablet comprising about 100 mg to about 500 mg (e.g., about 100 mg, about 150 mg, about 200 mg, about 250 mg, about 300 mg, about 350 mg, about 400 mg, about 450 mg, or about 500 mg) said additional antibiotic (e.g., amoxicillin).

The additional antibiotic (e.g., amoxicillin) may be administered before, together with, or after the administration of the compound I. In some embodiments, the additional antibiotic (e.g., amoxicillin) is administered together with the compound I to the patient.

The additional antibiotic (e.g., amoxicillin) may be administered before, together with, or after the administration of the acid blocker (e.g., the PPI, such as the rabeprazole sodium). In some embodiments, the additional antibiotic (e.g., amoxicillin) is administered together with the acid blocker (e.g., the PPI, such as the rabeprazole sodium) to the patient.

The additional antibiotic (e.g., amoxicillin) may be administered before, together with, or after the administration of the compound I and the acid blocker (e.g., the PPI, such as the rabeprazole sodium). In some embodiments, the additional antibiotic (e.g., amoxicillin) is administered together with the compound I and the acid blocker (e.g., the PPI, such as the rabeprazole sodium) to the patient.

Helicobacter pylori (H. pylori) Infection

In any aspect of the present disclosure, the Helicobacter pylori infection may be related to or caused by one or more drug resistant strains of Helicobacter pylori.

In some cases, the drug resistant Helicobacter pylori may be resistant to an antibiotic, such as one or more antibiotics selected from the group consisting of clarithromycin, amoxicillin, metronidazole, levofloxacin, tetracycline, furazolidone and rifabutin.

In some embodiments, the drug resistant Helicobacter pylori is resistant to rifabutin. In some embodiments, the drug resistant Helicobacter pylori is resistant to metronidazole. In some embodiments, the drug resistant Helicobacter pylori is resistant to rifabutin and metronidazole.

Drug Combination and Kit

The present disclosure also provides a drug combination and/or a kit.

The drug combination or the kit may further comprise an instruction for applying or practicing the method of the present disclosure.

The drug combination may be a drug product commercialized as a whole. In some cases, the drug combination comprises one or more separate products or components that are intended to function or be used together.

The drug combination or the kit of the present disclosure may be used for treating, ameliorating, reversing and/or preventing a Helicobacter pylori (H. pylori) infection in a patient in need thereof.

In some cases, the drug combination or the kit of the present disclosure may comprise one or more separately packaged daily dose drug combination unit. Each daily dose unit comprises a combination of drugs intended to be administered to a patient during one day. Each of the daily dose unit may comprise 1, 2, 3 or 4 single-dosing drug combination sets (or single administration drug combination sets). For example, the daily dose unit may comprise a morning drug combo set and an evening drug combo set, the morning drug combo set may comprise all the drugs to be administered after breakfast, and the evening drug combo set may comprise all the drugs to be administered after dinner.

In some embodiments, a single-dosing drug combination set comprises about 400 mg to about 600 mg of the compound I of the present disclosure or a pharmaceutically salt thereof, and about 10 mg to about 40 mg of the acid blocker (e.g., the PPI, such as the rabeprazole sodium) of the present disclosure.

In some embodiments, the drug combination or the kit comprises 7-14 of the separately packaged daily dose drug combination units.

In some embodiments, each of the single-dosing drug combination set also comprises about 100 mg to about 1000 mg the additional antibiotic (e.g., amoxicillin) of the present disclosure.

In some embodiments, each of the single-dosing drug combination set comprises 4-6 capsules of the compound I of the present disclosure, each capsule comprises about 100 mg of the compound I or a pharmaceutically acceptable salt thereof.

In some embodiments, each of the single-dosing drug combination set comprises 1 tablet (such as an enteric-coated tablet) of the acid blocker (e.g., the PPI, such as the rabeprazole sodium) of the present disclosure, each tablet comprises about 20 mg of the acid blocker.

In some embodiments, each of the single-dosing drug combination set comprises 2 capsules of the additional antibiotic (e.g., amoxicillin), and each capsule comprises about 500 mg of the additional antibiotic.

In some embodiments, each of the single-dosing drug combination set comprises 4 capsules of the additional antibiotic (e.g., amoxicillin), and each capsule comprises about 250 mg of the additional antibiotic.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); r.t., room temperature; and the like.

Example 1 Combination Therapy for Eradicating *H. pylori* Infection 40 asymptomatic healthy patients that are positive for *Helicobacter pylori* infection were admitted to the trial. The 40 patients were randomly allocated to four groups at a ratio of 1:1:1:1.

Different therapies were administered to the patients of each group according to the schedule below:

Group A:
Compound I capsule 200 mg/time (2 capsules, 100 mg/capsule), twice per day (BID); rabeprazole sodium enteric-coated tablet 20 mg/time (1 tablet, 20 mg/tablet), twice per day (BID)

Group B:
Compound I capsule 400 mg/time (4 capsules, 100 mg/capsule), twice per day (BID); rabeprazole sodium enteric-coated tablet 20 mg/time (1 tablet, 20 mg/tablet), twice per day (BID)

Group C:
Compound I capsule 600 mg/time (6 capsules, 100 mg/capsule), twice per day (BID); rabeprazole sodium enteric-coated tablet 20 mg/time (1 tablet, 20 mg/tablet), twice per day (BID)

Group D:
Compound I capsule 400 mg/time (4 capsules, 100 mg/capsule), twice per day (BID); rabeprazole sodium enteric-coated tablet 20 mg/time (1 tablet, 20 mg/tablet), twice per day (BID); amoxicillin capsule 1 g/time (4 capsules, 0.25 g/capsule), twice per day (BID)

All patients were admitted to the clinical research center 1 day before dosing (D-1 Day), randomly allocated to respective groups and completed examinations for safety and baseline indicators. From day 1 to day 14, respective therapies/drugs were orally administered to the patients within 30 minutes after breakfast and dinner. On day 15, the last dose was administered orally to the patients within 30 minutes after breakfast. During the trial, each patient was dosed for 29 times in total. All patients left the hospital after completing a safety tolerance assessment on day 17 and returned to the clinical research center for urea breath test (UBT) follow-up examination between days 44 and 50 to evaluate the effect of *Helicobacter pylori* eradication.

Blood samples of the patients were taken and analyzed according to the following schedule:
Day 1: within 30 mins after breakfast, 0.5 h, 1 h, 1.5 h, 2 h, 2.5 h, 3 h, 3.5 h, 4 h, 5 h, 6 h, 7 h, 8 h, 9 h, 10 h, 11 h and 12 h after breakfast, respectively (before the second dosing on day 1);
Day 3, 5, 7, 9, 11, 13 and 14: within 30 mins after breakfast;
Day 15: within 30 mins after breakfast, 0.5 h, 1 h, 1.5 h, 2 h, 2.5 h, 3 h, 3.5 h, 4 h, 5 h, 6 h, 7 h, 8 h, 9 h, 10 h, 11 h, 12 h, 24 h (Day 16) and 48 h (Day 17) after breakfast, respectively.

Whole blood was collected using vacuum blood collection tubes containing anticoagulants, 4 mL per tube, after which the plasma was centrifuged and the plasma sample was divided into two parts, stored in a −80° C. refrigerator, one part was used for pharmacokinetic analysis and the other part as backup.

The amount of Compound I, rabeprazole sodium and/or amoxicillin in the plasma was examined by LC-MS/MS.

The detection linear range was as below:

Compound I: Lower Limit Of Quantitation (LLOQ): 1.00 ng/mL; Upper Limit Of Quantitation (ULOQ): 1,000 ng/mL Rabeprazole sodium: LLOQ: 2.00 ng/mL; ULOQ: 1,000 ng/mL Amoxicillin: LLOQ: 40.0 ng/mL; ULOQ: 20,000 ng/mL.

Pharmacokinetics Evaluation

Plasma drug concentrations of various groups at different time points were determined, including: arithmetic mean, standard deviation, minimum, median, maximum, geometric mean, coefficient of variation, and coefficient of geometric variation.

The pharmacokinetic parameters calculated from the first and last administration were descriptively analyzed according to various trial groups, including: arithmetic mean, standard deviation, minimum value, median, maximum value, geometric mean, coefficient of variation, geometric coefficient of variation, etc. In addition, the accumulation index $AUC_{0-tau,\ ss}(D15)/AUC_{0-tau}(D1)$ was calculated. The average and individual drug-time curves were plotted linearly and semi-logarithmically. Variance analysis or non-parametric tests were performed on the pharmacokinetic parameters among the trial groups.

1) Pharmacokinetic Characteristics of Compound I and the Metabolite Thereof in Combination Therapy In groups A, B, C, and D, Compound I capsules were administered at doses of 200 mg BID, 400 mg BID, 600 mg BID, and 400 mg BID, respectively.

Compound I capsules combined with rabeprazole sodium enteric-coated tablets in each group (group A, B and C): after the first administration on day 1, the major pharmacokinetic parameters ($C_{max}$, $AUC_{0-tau}$, $AUC_{0-\infty}$) of Compound I increased with the increase of the dose of Compound I; the plasma concentrations of Compound I in each group showed a steady-state trend from the third day of continuous administration; after the last administration on day 15, the major pharmacokinetic parameters of Compound I ($C_{max,ss}$, $C_{min,ss}$, $C_{avg,ss}$, $AUC_{0-\infty,ss}$, $AUC_{0-tau,ss}$, $AUC_{0-last,ss}$) increased with the increase of the dose of Compound I, while $R_{ac}$ decreased, with only mild accumulation. Comparing group B and group D (i.e., administered the same amount of Compound I), no significant difference in the major pharmacokinetic parameters was observed, as shown in Table 1.

Comparing to the PK (pharmacokinetics) parameters of Compound I for 14 days of continuous administration, it can be seen that no significant difference was observed for the combination therapy (after combining with rabeprazole sodium and/or amoxicillin).

TABLE 1

| PK parameter | Group A (N = 10) | Group B (N = 10) | Group C (N = 10) | Group D (N = 10) |
| --- | --- | --- | --- | --- |
| Day 1 | | | | |
| $C_{max}$(ng/mL) | 176.360 ± 103.1865 | 457.800 ± 195.9647 | 773.600 ± 386.2297 | 426.000 ± 171.4410 |
| $AUC_{0-tau}$(h*ng/mL) | 417.246 ± 254.5521 | 1658.578 ± 923.2848 | 3187.476 ± 1880.9716 | 1422.919 ± 629.8686 |
| $AUC_{0-\infty}$(h*ng/mL) | 443.882 ± 277.0655 | 1801.654 ± 1024.7808 | 3492.992 ± 2107.0416 | 1506.350 ± 676.3607 |
| CL/F(L/h) | 584.464 ± 297.7728 | 284.393 ± 139.8369 | 225.457 ± 105.1488 | 309.858 ± 118.4103 |
| Vd/F(L) | 2999.727 ± 1580.9233 | 1269.501 ± 570.3610 | 1013.379 ± 557.5529 | 1386.297 ± 706.0455 |
| $t_{1/2}$(h) | 3.5887 ± 0.8330 | 3.3818 ± 1.4448 | 3.1538 ± 0.9616 | 3.0700 ± 0.7920 |
| $T_{max}$(h) | 2.75 (2.0, 5.0) | 4.5 (2.0, 6.0) | 5.0 (3.0, 6.0) | 3.0 (1.5, 5.0) |
| Day 15 | | | | |
| $t_{1/2,\,ss}$(h) | 7.7240 ± 1.8409 | 8.0843 ± 1.5967 | 9.1009 ± 0.9813 | 8.0961 ± 1.1311 |
| $T_{max,\,ss}$(h) | 3.0 (2.5, 6.0) | 5.0 (3.0, 5.0) | 4.0 (2.0, 6.0) | 4.5 (3.0, 6.0) |
| $C_{max,\,ss}$(ng/mL) | 184.120 ± 68.6538 | 496.000 ± 292.8682 | 738.810 ± 563.5177 | 476.000 ± 270.7890 |
| $AUC_{0-tau,\,ss}$(h*ng/mL) | 614.427 ± 222.9087 | 2026.604 ± 1107.3093 | 3171.957 ± 2291.7093 | 2213.361 ± 1517.3108 |
| $AUC_{0-last,\,ss}$(h*ng/mL) | 718.913 ± 279.9867 | 2489.403 ± 1344.2060 | 4091.311 ± 3233.1280 | 2682.568 ± 1820.6170 |
| $AUC_{0-\infty,\,ss}$(h*ng/mL) | 746.365 ± 278.8161 | 2519.614 ± 1355.6385 | 4175.049 ± 3308.2957 | 2711.905 ± 1829.5734 |
| $C_{min,\,ss}$(ng/mL) | 10.874 ± 5.3230 | 41.890 ± 27.3319 | 75.786 ± 70.7444 | 47.570 ± 37.0716 |
| $C_{avg,\,ss}$(ng/mL) | 51.202 ± 18.5757 | 168.884 ± 92.2758 | 264.330 ± 190.9758 | 184.447 ± 126.4426 |
| $CL/F_{ss}$(L/h) | 366.709 ± 132.2445 | 270.296 ± 174.2922 | 430.174 ± 632.2271 | 323.816 ± 283.5584 |
| $V/F_{ss}$(L) | 3832.518 ± 898.2771 | 3182.958 ± 2350.2525 | 5298.080 ± 7099.4315 | 3848.112 ± 3560.7135 |
| $R_{ac}$ | 1.71 ± 0.626 | 1.37 ± 0.661 | 1.05 ± 0.534 | 1.49 ± 0.766 |
| DF(%) | 342.34 ± 77.320 | 268.54 ± 66.200 | 252.93 ± 55.087 | 251.71 ± 52.180 |

Note:
Except for $T_{max}$, which is described using median (minimum, maximum), the remaining pharmacokinetic parameters are described using Mean ± SD 2) Pharmacokinetic Characteristics of Rabeprazole in the Combination Therapy In the combined therapy of groups A, B, C and D, rabeprazole sodium enteric-coated tablets were administered at a dose of 20 mg BID.

Compound I capsules combined with rabeprazole sodium enteric-coated tablets in each dose group (group A, group B, group C): after the first administration on day 1, with the increase of the dose of Compound I in the combination therapy, the major pharmacokinetic parameters ($C_{max}$, $AUC_{0-tau}$, $AUC_{0-\infty}$) of rabeprazole also increased; the plasma concentration of rabeprazole in each group showed a steady-state trend from the third day of continuous administration; after the last administration on day 15, with the increase of the dose of Compound I in the combination therapy, $C_{max,\,ss}$ of rabeprazole initially increased and then decreased, and no significant change was observed for other major pharmacokinetic parameters, and there was no significant accumulation.

These results suggest that after 14 days of continuous administration, combination with Compound I may mildly affect the peak concentration of rabeprazole. Results from group B and group D were compared, it was found that amoxicillin had no significant effect on the major pharmacokinetic parameters of rabeprazole after the first administration on day 1 and after the last administration on day 15.

3) Pharmacokinetic Characteristics of Amoxicillin in Combination Therapy

In Group D, compared to the first administration on day 1, there was no significant difference in the pharmacokinetic parameters of amoxicillin after the last administration on day 15, only mild accumulation was observed, and the plasma concentration showed a steady-state trend from the 3rd day of continuous administration.

Taken together, it can be seen that the major pharmacokinetic parameters of Compound I increased with the increase of the dose of Compound I. After 14 days of continuous administration, rabeprazole and amoxicillin had no significant effect on the pharmacokinetic profile of Compound I.

Safety Evaluation

The safety tolerance assessment incudes assessment of adverse events (AE), serious adverse events (SAE), drug-related AEs, and AEs leading to withdrawal.

The number and incidence of all adverse events were summarized according to the respective trial group, systemic organ classification and preferred terminology.

By trial group, according to the CTCA 5.0 rating, the list describes the incidence of adverse events in each trial group (occurred in each trial group alone, in 2 groups or 3 groups).

By systemic organ classification and preferred terminology, the list describes the number and incidence of adverse events in each trial group, depending on the severity and relevance to the drug for investigation.

By trial group, the mean, standard deviation, median, minimum and maximum values of vital signs (blood pressure, breathing, pulse and body temperature) and laboratory indicators before and after drug administration were calculated, and when necessary, paired t-test or non-parametric test were used for before-and-after comparison.

SAE and Suspected Unintended Serious Adverse Reactions (SUSAR) were listed separately.

A total of 41 patients were enrolled, 40 patients completed the trial, and all 40 patients who completed the trial were included in the safety analysis set. 57 TEAE episodes occurred in 27 patients with an incidence of 67.5%, of which 25 patients had 53 TEAEs associated with the combination therapy of the present disclosure, with a total incidence of 62.5% (Table 2). Most of the drug-related adverse events were grade 1, 6 patients had 7 cases of grade 2, and only 1 patient had a severity of grade 3 (hypertriglyceridemia), except for 1 case of grade 2 rash with the administration of the combination therapy of the present disclosure, the remaining drug-related AEs had not been intervened and had fully recovered. There was no grade 3 or higher adverse events in the entire trial, no adverse events that led to discontinuation of the combination therapy, no adverse reactions that led to patients dropping out of the trial, no SAE, and no AE leading to death.

TABLE 2

Incidence of AEs

| | Group A (N = 10) | Group B (N = 10) | Group C (N = 10) | Group D (N = 10) | Total (N = 40) |
|---|---|---|---|---|---|
| TEAE | 60% (6/18) | 80% (8/12) | 50% (5/8) | 80% (8/19) | 67.5% (27/57) |
| Drug related TEAE | 60% (6/18) | 70% (7/9) | 50% (5/8) | 70% (7/17) | 62.5% (25/52) |

Note:
% = Number of patients with adverse events in the group/Total number of patients in the group.
Incidence of ≥15% of common adverse events associated with the combination therapy:
Group A: elevated serum creatinine (30%), hyperglycemia (20%);
Group B: elevated hemobilirubin (20%), hyperglycemia (20%);
Group C: absent;
Group D: elevated alanine aminotransferase (20%), elevated aspartic acid aminotransferase (20%), hypertriglyceridemia (20%), hyperuricemia (20%), rash (20%), papules (20%).

No significant dose correlation was observed in Group A, B or C, and no significant difference was observed between Group B and D (with the same dose of Compound 1).

During the trial, specific attention was paid to the following adverse events expected to be correlated with the combination treatment of the study:

(1) A total of 9 cases of elevated serum creatinine occurred, with an incidence rate of 15%, including 4 cases in group A, 1 case in group B, 2 cases in group C, and 2 cases in group D. The decrease in renal creatinine clearance occurred in 4 cases, with an incidence rate of 7.5%, 2 cases in group A, 1 case in group C, and 1 case in group D. Among them, a group A patient had a decrease in renal creatinine clearance and an increase in serum creatinine. All adverse events of elevated serum creatinine and decreased renal creatinine clearance in this trial were of grade 1 level, which were basically transient, and no treatment measures were taken during the trial, and they were fully recovered. No dosage correlation was observed.

(2) A total of 7 cases of elevated transaminases occurred, of which 1 case in group A had elevated alanine aminotransferase, 1 case in group C and 2 cases in group D had elevated alanine aminotransferase, accompanied by an increase of aspartic acid aminotransferase, AE began from D6 or D8, but it began later in group C (from D12). The severity was all grade 1, basically transient, no treatment measures were taken during the trial, and all have been fully recovered.

(3) A total of 10 cases of skin abnormalities occurred. Among them, 8 cases of skin abnormalities were drug-related, manifested by rash, papules, and itching. 1 case in group A had rash. In group B, 1 case had itching and 1 case had rash. In group D, 1 case had itching, papules, and rash; 1 case had a large area of rash and developed grade 2 symptoms, which got better after antihistamine treatment; and 1 case had papules. In group B, 1 case had grade 2 eczema/lichen, which was determined to be unrelated the combination therapy of the present study, According to CTC AE 5.0 rating: 46 cases of grade 1 adverse events occurred, 10 cases of grade 2 adverse events occurred. Among the drug-related AEs, 45 were grade 1, and 6 cases were grade 2 (1 had reduction in white blood cells, 3 cases had reduction in neutrophil, 1 case had hypertriglyceridemia, and 1 case had rash). 3 grade 3 AEs occurred in group B (with 1 case of hypertriglyceridemia). No AEs above grade 3 occurred. The AEs were basically transient, and no specific treatment was required. Actually, only 1 case of grade 2 rash was treated with combination therapy, the rest of the drug-related AEs have not been intervened and have fully recovered.

Unexpected adverse reactions: during the trial, a total of 7 cases (15.0%) of unexpected adverse reactions occurred, with 6 cases (12.5%) of hyperglycemia, and 1 case of eyelid itching, all of which were determined to be related to the combination therapy of the present disclosure, the severity was grade 1, and all of them recovered without treatment.

The results show that the combination therapy of the present disclosure, after being administered continuously for 14 days in asymptomatic healthy people with positive *Helicobacter pylori* infection, had good safety and tolerability characteristics.

Efficacy Evaluation

The initial analysis of eradication effect was based on the full data set, which is defined as all patients who were randomly selected and received at least one dose of the trial combination therapy.

The eradication effects in each trial group were evaluated by UBT tests (negative or positive) conducted at the baseline time point, on day 8 after drug administration, day 16 after drug administration and day 44-50 of follow-up visit. Descriptive analysis was done using frequency (percentage), and comparison between groups was made. Fisher precision test was used to conduct between-group comparison analysis. As an aid to the analysis, the UBT values were listed as mean, standard deviation, median, minimum, maximum, and deviation from the baseline.

After 14 days of continuous administration of the combination therapy of the present disclosure, and to the follow-up period (day 44 to day 50), the negative rate of UBT results increased with the increase of the dose of Compound I combined with rabeprazole sodium enteric-coated tablets (i.e., group A, B and C). In group D, the eradication rate of *H. pylori* was as high as 80%, as can be seen in Table 3.

TABLE 3

|  | Group A (N = 10) n(%) | Group B (N = 10) n(%) | Group C (N = 10) n(%) | Group D (N = 10) n(%) |
|---|---|---|---|---|
| Baseline | 0 (0.0) | 0 (0.0) | 0 (0.0) | 0 (0.0) |
| Day 8 | 7 (70.0) | 10 (100.0) | 8 (80.0) | 7 (70.0) |
| Day 16 | 3 (30.0) | 5 (50.0) | 6 (60.0) | 10 (100.0) |
| Follow up period (Day 44~50) | 0 (0.0) | 3 (30.0) | 4 (40.0) | 8 (80.0) |

Note:
n: the number of patients with UBT negative results.

It can be seen that the combination therapy of the present disclosure could be used to successfully eradicate *H. pylori* infection.

Example 2 Combination Therapy for Eradicating *H. pylori* Infection

In this example, 80 patients that are positive for *Helicobacter pylori* infection were admitted to the trial. The 80 patients were randomly allocated to 5 groups at a ratio of 2:2:1:1:2, including 4 treatment groups and 1 control group, and the dosage regimen is shown in Table 4.

TABLE 4

|  |  | Dosage Regimen | Frequency and Duration | Number of patients |
|---|---|---|---|---|
| Treatment Groups | A | Compound I capsule 400 mg, rabeprazole sodium enteric-coated tablet 20 mg, amoxicillin capsule 1 g | BID × 14 day | 20 |
|  | B | Compound I capsule 600 mg, rabeprazole sodium enteric-coated tablet 20 mg, amoxicillin capsule 1 g | BID × 14 day | 20 |
|  | C | Compound I capsule 600 mg, rabeprazole sodium enteric-coated tablet 20 mg | TID × 14 day | 10 |
|  | D | Compound I capsule 600 mg, rabeprazole sodium enteric-coated tablet 20 mg, amoxicillin capsule 1 g | TID × 7 day | 10 |
| Control Group |  | Rabeprazole sodium enteric-coated tablet 20 mg, amoxicillin capsule 1 g | BID × 14 day | 20 |

All patients were admitted to a clinical center 1 day (D-1) before dosing, completed examinations for safety indicators and baseline, and were randomly allocated to one of the groups.

Group A, B, C and Control Group Study Schedule (Continuous Administration for 14 Days):

Patients were administered with the combination therapy daily according to the dosing regimen of the respective group from day 1 to day 14, and the last dose was administered in the morning of day 15. Pharmacokinetic blood samples were collected at the scheduled time point during the trial and patiented to a safety tolerance assessment and $^{14}C$ UBT test. All patients left the hospital after completing the safety tolerance assessment and PK blood collection on the $17^{th}$ day (day 17), and returned to the research institution for follow-up visits from the $44^{th}$ to $50^{th}$ day (day 44-day 50). Follow-up of adverse events and laboratory abnormalities continued until the patients completely recovered or returned to baseline levels or stable states. Safety tolerance assessment, and $^{14}C$ UBT tests were performed to assess *H. pylori* eradication effects.

Group D Study Schedule (Continuous Administration for 7 Days):

Patients were administered with the combination therapy daily according to the dosing regimen of the respective group from day 1 to day 7, and the last dose was administered in the morning of day 8. Pharmacokinetic blood samples were collected at the scheduled time point during the trial and patiented to a safety tolerance assessment and $^{14}C$ UBT test. All patients left the hospital after completing the safety tolerance assessment and PK blood collection on the $10^{th}$ day (day 10), and returned to the research institution for follow-up visits from the $37^{th}$ to $43^{rd}$ day (day 37-day 43). Follow-up of adverse events and laboratory abnormalities continued until the patients completely recovered or returned to baseline levels or stable states. Safety tolerance assessment, and $^{14}C$ UBT tests were performed to assess *H. pylori* eradication effects.

The administration regimen was as follows:
Group A, Group B and Control Group:
Twice per day, the combination therapy was administered orally within 30 mins after breakfast and dinner, respectively, and the combination therapy was administered for 14 days consecutively. On day 15, the last administration was provided within 30 mins after breakfast. Each patient was administered for 29 times in total.

Group C and Group D:
Three times per day, and two administrations were separated by about 8 hours.

For group C, the combination therapy was administered for 14 days consecutively. On day 15, the last administration was provided after breakfast. Each patient was administered for 43 times in total.

For group D, the combination therapy was administered for 7 days consecutively. On day 8, the last administration was provided after breakfast. Each patient was administered for 22 times in total.

The specific dosage and regimen is provided in Table 5.

TABLE 5

|  |  |  | Units/time |  |  |  |
|---|---|---|---|---|---|---|
| Groups |  | Frequency | Compound I (100 mg/capsule) | Rabeprazole sodium enteric-coated tablet (20 mg/table) | Amoxicillin capsule (0.5 g/capsule) | Duration (day) |
| Treatment group | A | BID | 4 | 1 | 2 | 14 |
|  | B | BID | 6 | 1 | 2 | 14 |
|  | C | TID | 6 | 1 | — | 14 |
|  | D | TID | 6 | 1 | 2 | 7 |
| Control Group |  | BID | — | 1 | 2 | 14 |

Pharmacokinetics Evaluation

PK Collection Time Point:

Blood samples for PK analysis were collected at the following time points:

1) For group A, group B and control group:

Day 1: within 30 mins before administration, 0.5 h, 1 h, 1.5 h, 2 h, 2.5 h, 3 h, 3.5 h, 4 h, 5 h, 6 h, 7 h, 8 h, 9 h, 10 h, 11 h, 12 h after administration (before the second administration of the day);

Day 3, 5, 7, 9, 11, 13 and 14: within 30 mins before administration:

Day 15: within 30 mins before administration, 0.5 h, 1 h, 1.5 h, 2 h, 2.5 h, 3 h, 3.5 h, 4 h, 5 h, 6 h, 7 h, 8 h, 9 h, 10 h, 11 h, 12 h, 24 h (day 16) and 48 h (day 17) after administration.

2) For group C:

Day 1: within 30 mins before administration, 0.5 h, 1 h, 1.5 h, 2 h, 2.5 h, 3 h, 3.5 h, 4 h, 5 h, 6b, 7 h and 8 h after administration (before the second administration of the day);

Day 3, 5, 7, 9, 11, 13 and 14: within 30 mins before administration:

Day 15: within 30 mins before administration, 0.5 h, 1 h, 1.5 h, 2 h, 2.5 h, 3 h, 3.5 h, 4 h, 5 h, 6 h, 7 h, 8 h, 9 h, 10 h, 11 h, 12 h, 24 h (day 16) and 48 h (day 17) after administration.

3) For group D:

Day 1: within 30 mins before administration, 0.5 h, 1 h, 1.5 h, 2 h, 2.5 h, 3 h, 3.5 h, 4 h, 5 h, 6 h, 7 h and 8 h after administration (before the second administration of the day);

Day 3, 5, 7: within 30 mins before administration:

Day 8: within 30 mins before administration, 0.5 h, 1 h, 1.5 h, 2 h, 2.5 h, 3 h, 3.5 h, 4 h, 5 h, 6 h, 7 h, 8 h, 9 h, 10 h, 11 h, 12 h, 24 h (day 9) and 48 h (day 10) after administration.

PK Blood Sample Treatment:

Whole blood was collected using vacuum blood collection tubes containing anticoagulants, 4 mL per tube, after which the plasma was centrifuged and the plasma sample was divided into two parts, stored in a $-80°$ C. refrigerator, one part was used for pharmacokinetic analysis and the other part as backup.

For the first administration, PK analysis included at least the following parameters: $T_{max}$, $C_{max}$, $t_{1/2}$, $AUC_{0-\infty}$, $AUC_{0-tau}$, $V_d/F$ and $CL/F$.

For group A, group B and control group, two administrations were separated by 12 hours. For group C and group D, two administrations were separated by 8 hours.

For the last administration, PK analysis included at least the following parameters: $T_{max,ss}$, $C_{max,ss}$, $C_{min,ss}$, $C_{avg,ss}$, $t_{1/2,ss}$, $AUC_{0-\infty,ss}$, $AUC_{0-last,ss}$, $AUC_{0-tau,ss}$, $V_d/Fss$, $CL/Fss$, $DF(=100\times(C_{max,s}-C_{min,ss})/C_{avg,ss}))$ and $R_{ac}$ (group A, B, C and control group: $AUC_{0-tau,ss}$ on day 15/$AUC_{0-tau}$ on day 1; group D: $AUC_{0-tau,ss}$ on day 8/$AUC_{0-tau}$ on day 1).

Safety Evaluation

Safety of the treatment was evaluated according to CTC AE 5.0 ratings.

Observed any adverse event (AE) that occurred during the trial in all patients, recorded their clinical characteristics, severity, occurrence time, end time, treatment measures and outcome, and determined the correlation of the AEs with the combination therapy of the present disclosure.

The safety tolerance evaluation mainly includes adverse events (AE), physical examination, vital signs (blood pressure, pulse, breathing and body temperature), clinical laboratory tests (blood routine, urine routine, blood biochemistry, coagulation function) and ECG etc.

Efficacy Evaluation

Group A, B, C and Control Group:

Patients were examined with $^{14}C$ UBT test during the screening period (D-14~D-2), baseline period (D-1), day 8 (D8), day 16 (D16) and days 44~50 (D44~D50). The test was done fasting before breakfast to determine the effects of H. pylori eradication in each group.

Group D:

Patients were examined with $^{14}C$ UBT test during the screening period (D-14~D-2), baseline period (D-1), day 8 (D8) and days 37~day 43 (D37~D43). The test was done fasting before breakfast to determine the effects of H. pylori eradication in each group.

Statistical Analysis

Definition of Data Set:

Full Analysis Set (FAS): refers to all randomized patients who have been administered with the combination therapy of the present disclosure at least once;

Modified Intentionality Analysis Set (mITT): refers to all randomized patients who underwent a $^{14}C$ UBT test on days 28 to 34 after the last administration;

Protocol-compliant Set (PP): refers to patients who have not experienced major protocol violations: randomized and treated with more than 80% (including 80%) of the total amount of the drug expected to be used in the investigation, and who were tested for $^{14}C$ UBT on days 28 to 34 after the last administration;

Safety Analysis Set (SS): refers to the patients who have entered the trial and have been administered the combination therapy of the present disclosure at least once;

Pharmacokinetic Concentration Analysis Dataset (PKCS): refers to all enrolled patients who have been administered with the combination therapy of the present disclosure and had at least one PK concentration observation;

Pharmacokinetic Parameter Analysis Dataset (PKPS): Refers to all enrolled patients who have been administered with the combination therapy of the present disclosure and had at least one PK parameter observation data point.

Demographic Analysis:

Demographic analysis was based on Full Analysis Set (FAS). Descriptive statistical analysis of all demographics (age, sex, weight, height, BMI, ethnicity, etc.) and baseline characteristics, based on the measurement of the last valid data before the administration of the combination therapy of the present disclosure.

Evaluation of the Eradication Effect of Helicobacter pylori:

The eradication effect analysis was performed with the Full Analysis Set (FAS), based on the results of four $^{14}C$ UBT tests (negative or positive) in group A, group B, group C, and control groups at baseline, on day 8, day 16, and follow-up days 44 to 50, and three $^{14}C$ UBT test results (negative or positive) in group D at baseline, on day 8, and follow-up days 37 to 43. Inter-group comparison analysis was performed, mainly based on the comparison between the treatment group and the control group, as well as comparisons between the treatment groups. The eradication rate of Helicobacter pylori is defined as the proportion of patients with negative $^{14}C$ UBT test results on days 28 to 34 after the last administration. At the same time, the eradication rate of Helicobacter pylori in each group was calculated for the mITT analysis set and PP analysis set, and sensitivity analysis was performed.

TABLE 6

UBT test results of treatment group A

| Period | UBT results | Group A (FAS) (N = 20) n(%) | Group A (mITT) (N = 19) n(%) |
|---|---|---|---|
| Day 8 after administration | Negative | 18 (90.0) | 18 (94.7) |
| | Positive | 1 (5.0) | 1 (5.3) |
| Day 16 after administrtion | Negative | 18 (90.0) | 18 (94.7) |
| | Positive | 1 (5.0) | 1 (5.3) |
| Follow up period (Day 44~Day 50) | Negative | 18 (90.0) | 18 (94.7) |
| | Positive | 1 (5.0) | 1 (5.3) |

Note:
N: the total number of patients within each analysis set; n: the number of patients with UBT negative results.
There is one patient who withdrew early from the study and was not counted in the mITT population.

Table 6 summarizes the efficacy evaluation of combination therapy of compound I, rabeprazole sodium and amoxicillin as shown in the treatment group A of Table 5. It can be seen that the eradication rate (mITT set) of *Helicobacter pylori* has reached almost 95% (94.7%), which significantly surpasses the disclosed eradication rate of the first-line therapeutic option of bismuth quadruple therapy (72.9%).

Safety Analysis:

The safety tolerance evaluation analysis is mainly based on descriptive statistical summary. AE, adverse events during treatment (TEAE), serious adverse events (SAE), drug-related AEs, and AEs leading to withdrawal from the trial were pooled.

By different groups, systemic organ classifications and preferred terminology, the list summarizes the number, frequency and incidence of all adverse events.

By different groups, the list describes the number and incidence of adverse events at all levels in each group, depending on the CTCAE classification.

By systemic organ classification and preferred terminology, the list describes the number and incidence of adverse events in each group, depending on severity and relevance to the combination therapy.

By systemic organ classification and preferred terminology, the list describes the number and incidence of common adverse events in each group.

By different groups, laboratory test results that were normal before the test but abnormal after treatment are described.

By different groups, the mean, standard deviation, median, minimum and maximum values of vital signs (blood pressure, breathing, pulse and body temperature) and laboratory indicators before and after administration were calculated, and when necessary, paired t-tests or non-parametric tests were used for pre- and post-comparison.

SAE and suspected unintended serious adverse reactions (SUSAR) were listed separately.

Pharmacokinetic Analysis:

The plasma concentration data was estimated and analyzed by Phoenix WinNolin software for the pharmacokinetic parameters of the non-AV model, the PK concentration data was analyzed by PKCS data, and the major pharmacokinetic parameters were calculated by PKPS data. Patients with severe deviations from the study protocol were excluded from pharmacokinetic analysis.

The results of the major pharmacokinetic parameters were summarized by sample size, arithmetic mean, standard deviation, coefficient of variation, median value, minimum value, maximum value, and geometric mean and geometric coefficient of variation by different groups. The major pharmacokinetic parameters include: PK parameters for first administration, such as $T_{max}$, $C_{max,ss}$, $t_{1/2}$, $AUC_{0-\infty}$, $AUC_{0-tau}$, Vd/F, CL/F; PK parameters for last administration, including $T_{max,ss}$, $C_{max,ss}$, $C_{min,ss}$, $C_{avg,ss}$, $t_{1/2,ss}$, $AUC_{0-last,ss}$, $AUC_{0-tau,ss}$, $AUC_{0-\infty,ss}$, $V/F_{ss}$, $CL/F_{ss}$, Rac, DF etc.

Example 3 Comparison of Different Dosage Forms

Dissolution profiles were compared using Compound I tablets (batch No.: T01-22012, strength: 400 mg) and Compound I capsules (batch No.: CT-22C077, strength: 100 mg). In the test, 4 capsules were loaded into the sink basket and put into the same dissolution cup at the same time so that the total dose was the same as that of the tablets, all of which were 400 mg. Each medium was tested in triplicate in parallel for each dosage form, and the dissolution comparison data for capsules and tablets are shown in the following tables.

TABLE 7

Comparison of tablet and capsule dissolution curve data (FeSSGF simulated gastric (fed condition) buffer at pH 5.0)

| Batch No./dosage form/strength | Cumulative dissolution % at the time point of detection | | | | | | | |
|---|---|---|---|---|---|---|---|---|
| | 0 min | 10 min | 15 min | 20 min | 30 min | 45 min | 60 min | 90 min |
| CT-22C077/Capsule/100 mg | 0 | 7 | 18 | 28 | 41 | 48 | 51 | 55 |
| T01-22012/tablet/400 mg | 0 | 20 | 25 | 29 | 34 | 40 | 43 | 51 |

Test method: The dissolution medium was FeSSGF gastric (simulation of fed condition) buffer at pH 5.0; samples were taken at 10, 15, 20, 30, 45, and 60 min at 50 rpm, and then at 250 rpm for 30 min.

TABLE 8

Comparison of tablet and capsule dissolution curve data (pH 4.5 sodium acetate buffer containing 0.5% Tween-80)

| Batch No./dosage form/strength | Cumulative dissolution % at the time point of detection | | | | | | | |
|---|---|---|---|---|---|---|---|---|
| | 0 min | 10 min | 15 min | 20 min | 30 min | 45 min | 60 min | 90 min |
| CT-22C077/Capsule/100 mg | 0 | 15 | 37 | 48 | 57 | 63 | 69 | 84 |
| T01-22012/tablet/400 mg | 0 | 30 | 36 | 42 | 50 | 59 | 63 | 78 |

Test method: The dissolution medium was pH 4.5 sodium acetate buffer containing 0.5% Tween-80; samples were taken at 10, 15, 20, 30, 45 and 60 minutes at 50 rpm, and then at 250 rpm for 30 minutes.

TABLE 9

Comparison of tablet and capsule dissolution curve data
(pH 4.5 sodium acetate buffer containing 0.5% Tween-80)

| Batch No./dosage form/strength | Cumulative dissolution % at the time point of detection | | | | | | | |
|---|---|---|---|---|---|---|---|---|
| | 0 min | 10 min | 15 min | 20 min | 30 min | 45 min | 60 min | 90 min |
| CT-22C077/Capsule/100 mg | 0 | 44 | 57 | 63 | 67 | 73 | 77 | 82 |
| T01-22012/tablet/400 mg | 0 | 41 | 52 | 58 | 66 | 73 | 77 | 83 |
| T02-22012/tablet/300 mg | 0 | 30 | 48 | 59 | 68 | 75 | 79 | 86 |

Test method: The dissolution medium was pH 4.5 sodium acetate buffer containing 0.5% Tween-80; samples were taken at 10, 15, 20, 30, 45 and 60 minutes at 75 rpm, and then at 250 rpm for 30 minutes.

From the above data, it can be seen that in combination with the clinical use of Compound I (fed condition in combination with proton pump inhibitors) and the characteristics of rapid release in the stomach and absorption in the intestine, it was mainly examined using dissolution media that mimic the dissolution and release of the drug in vivo, such as pH 4.5 buffer and FeSSGF gastric (fed condition) buffer pH 5.0.

The results show that the dissolution of Compound I in both media was low due to the low solubility of drug substance, and then the method was optimized by adding 0.5% of surfactant Tween-80 in pH 4.5 media, and the dissolution was improved, and the dissolution trends of both dosage forms in these two media were basically similar.

Due to the large tablet weight of this product, there was an accumulation of insoluble excipients microcrystalline cellulose during the dissolution process, so the speed in the dissolution method was increased from 50 rpm to 75 rpm, and the results showed that the dissolution trend in this condition was similar to that of pH 4.5 buffer (for both 300 mg and 400 mg strength tablet), and only after 15 minutes the dissolution rate of the capsules was slightly faster than that of the tablets.

Figure 2:
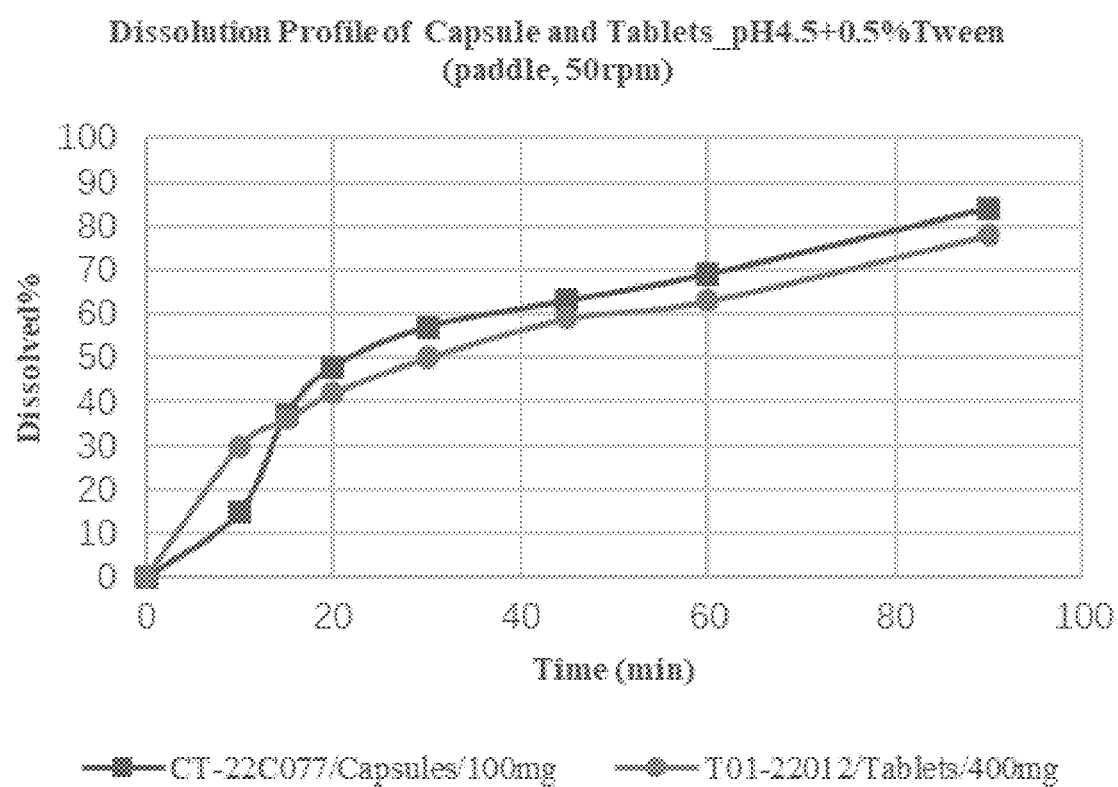
Figure 3:
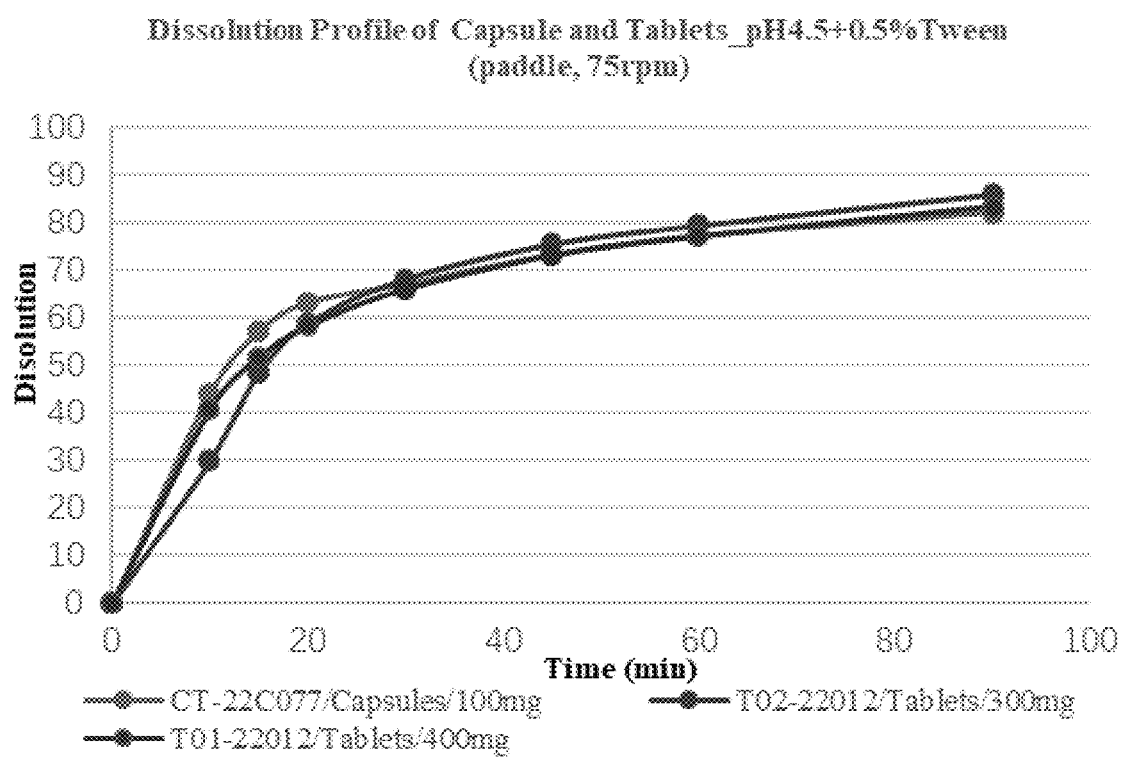

The results are shown in FIG. 1-3. It can be seen that the dissolution profiles of different dosage forms are similar.

While exemplary embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for treating, ameliorating, and/or reversing a *Helicobacter pylori* (*H. pylori*) infection in a patient in need thereof, comprising administering to said patient:

an effective amount of compound I 4-Deoxy-3,4-(1H)-imidazo-(2,5-dihydro)rifamycin, or a pharmaceutically acceptable salt thereof; an effective amount of an additional antibiotic, and an effective amount of an acid blocker, wherein said compound I is administered to said patient at a dose of about 400 mg to about 600 mg, twice per day (BID) or three times per day (TID), wherein said compound I is a compound of Formula 2

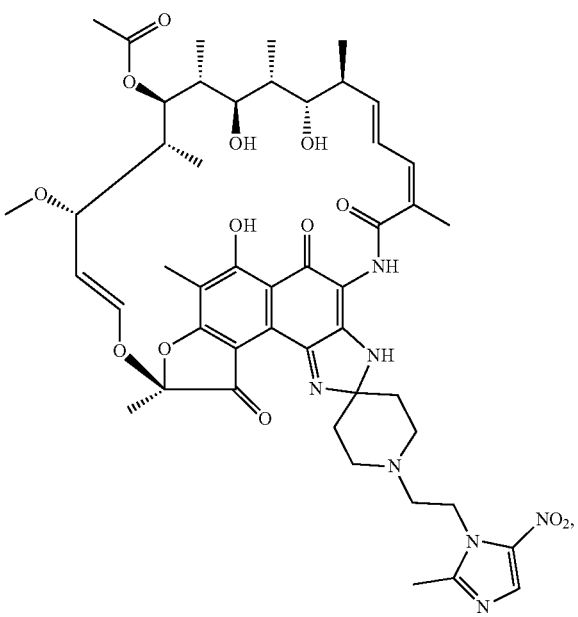

Formula 2 wherein an effective amount of said acid blocker is at a dose of about 10 mg to about 20 mg, and said acid blocker is proton pump inhibitor (PPI); and, wherein an effective amount of said additional antibiotic is twice per day (BID) or three times per day (TID), for 7-14 consecutive days; and said additional antibiotic is amoxicillin.

2. The method of claim 1, wherein said compound I is administered to said patient for 7-14 consecutive days.

3. The method of claim 1, wherein said compound I is administered in one or more dosage units, and each said dosage unit comprises about 100 mg to about 400 mg of said compound I.

4. The method of claim 1, wherein said compound I is administered as a capsule or a tablet.

5. The method of claim 1, wherein said acid blocker is administered to said patient at a dose of about 10 mg to about 40 mg, twice per day (BID) or three times per day (TID).

6. The method of claim 1, wherein said acid blocker is administered to said patient for at least 7-14 consecutive days.

7. The method of claim 1, wherein said acid blocker is administered as an enteric-coated tablet.

8. The method of claim 7, wherein each said enteric-coated tablet comprises about 10 mg to about 20 mg of said acid blocker.

9. The method of claim 1, wherein said acid blocker is selected from the group consisting of: rabeprazole sodium, esomeprazole magnesium, omeprazole, lansoprazole, pantoprazole sodium and ilaprazole.

10. The method of claim 1, wherein said additional antibiotic is administered to said patient at a dose of about 100 mg to about 1000 mg, twice per day (BID) or three times per day (TID).

11. The method of claim 1, wherein said additional antibiotic is administered to said patient for 7-14 consecutive days.

12. The method of claim 1, wherein said *Helicobacter pylori* is resistant to one or more antibiotics selected from the group consisting of clarithromycin, amoxicillin, metronidazole, levofloxacin, tetracycline, furazolidone and rifabutin.

13. A drug combination, comprising an effective amount of compound I 4-Deoxy-3,4-(1H)-imidazo-(2,5-dihydro)rifamycin, or a pharmaceutically acceptable salt thereof; an effective amount of an acid blocker, and an effective amount of an additional antibiotic, wherein said acid blocker is a proton pump inhibitor (PPD), said compound I is a compound of Formula 2

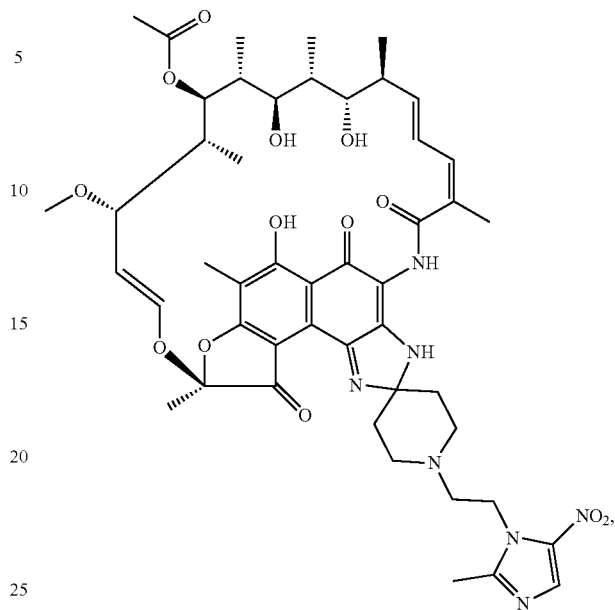

Formula 2 and
wherein said additional antibiotic is amoxicillin.

14. A kit, comprising the drug combination of claim 13.

* * * * *